United States Patent [19]

Arimitsu et al.

[11] Patent Number: 4,758,600

[45] Date of Patent: Jul. 19, 1988

[54] PROCESS FOR THE MANUFACTURE OF ETHANOL

[75] Inventors: Satoshi Arimitsu, Sagamihara; Katsumi Yanagi; Hitomi Hosono, both of Yokohama; Toshihiro Saito, Machida; Kazuaki Tanaka, Yokkaichi; Yuji Onda, Niigata; Kazuo Takada, Sagamihara; Keiji Mitarai, Sagamihara; Nobuyuki Taniguchi, Sagamihara; Yoshimitsu Ishii, Atsugi; Takakazu Fukushima, Sagamihara, all of Japan

[73] Assignee: Agency of Industrial Science and Technology, Tokyo, Japan

[21] Appl. No.: 941,072

[22] Filed: Dec. 12, 1986

Related U.S. Application Data

[63] Continuation-in-part of Ser. No. 824,955, Jan. 31, 1986, abandoned.

[30] Foreign Application Priority Data

| Feb. 2, 1985 | [JP] | Japan | 60-17723 |
| Feb. 2, 1985 | [JP] | Japan | 60-17724 |
| Sep. 9, 1985 | [JP] | Japan | 60-197789 |
| Sep. 9, 1985 | [JP] | Japan | 60-197792 |

[51] Int. Cl.$^4$ .............................. C07C 27/06
[52] U.S. Cl. ................. 518/713; 518/701; 518/714; 518/716; 518/707; 502/302; 502/305; 502/306; 502/326
[58] Field of Search ............... 518/701, 713, 716, 714, 518/707

[56] References Cited

U.S. PATENT DOCUMENTS

| 4,235,298 | 11/1980 | Bartley et al. | 518/716 |
| 4,298,354 | 11/1981 | Hardman et al. | |
| 4,327,190 | 4/1982 | Ball et al. | |
| 4,459,369 | 7/1984 | Passariello | |
| 4,537,909 | 5/1985 | Lin et al. | |

FOREIGN PATENT DOCUMENTS

| 60-32724 | 2/1985 | Japan | 518/716 |
| 60-32733 | 2/1985 | Japan | 518/716 |

Primary Examiner—Howard T. Mars
Attorney, Agent, or Firm—Oblon, Fisher, Spivak, McClelland & Maier

[57] ABSTRACT

Ethanol is prepared with high selectivity by the catalytic reaction of carbon monoxide and hydrogen. The catalyst composition comprises:

(A) catalyst component consisting of
 (a) a rhodium component,
 (b) a lithium component, and
 (c) a component of at least one element selected from the group consisting of iridium, manganese, scandium, mangesium, yttrium, ytterbium, lutecium, vanadium and chromium; and (B) catalyst component, which is supported on a separate carrier from said (A) catalyst component, being selected from the group consisting of
 (a) an iron component and a component of at least one element selected from the group consisting of iridium and palladium,
 (b) a molybdenum component and a component of at least one element selected from the group consisting of iridium and palladium,
 (c) an iron component, a molybdenum component and a component of at least one element selected from the group consisting of iridium and palladium, and
 (d) a copper component and optionally a component of at least one element selected from the group consisting of zinc and chromium.

10 Claims, No Drawings

PROCESS FOR THE MANUFACTURE OF ETHANOL

This application is a continuation-in-part of Ser. No. 824,955, filed Jan. 31, 1986, now abandoned.

BACKGROUND OF THE INVENTION

1. Field of the Invention

This invention relates to a process for the manufacture of ethanol by reaction of carbon monoxide with hydrogen in the presence of a novel catalyst composition.

2. Description of the Prior Art

Oxygen-containing compounds having two carbon atoms such as ethanol and acetaldehyde have hitherto been manufactured according to petrochemical processes using naphtha as a raw material. However, the recent sharp rise in crude oil price has caused a significant increase in the production cost of these carbon compounds and it has become necessary to employ a different raw material.

In this connection, investigations were carried out in various processes for the manufacture of oxygen-containing compounds having two carbon atoms from a mixed gas comprising carbon monoxide and hydrogen, both of which are available abundantly and inexpensively.

As a result, various processes became known wherein a mixed gas comprising carbon monoxide and hydrogen is subjected to reaction in the presence of a catalyst containing rhodium as an essential component and further containing metals such as manganese, titanium, zirconium and iron or their oxides to selectively manufacture oxygen-containing compounds having two carbon atoms, (e.g., GB Patent Nos. 1,501,891, 1,501,892 and 1,549,437; U.S. Pat. Nos. 4.463,105; etc.)

In these processes, however, hydrocarbons such as methane are generated in large amounts as by-products and the selectively of the oxygen-containing compounds is low or, when the selectively of the oxygen-containing compounds is high, the yield of these compounds is very low. Further, the yield of desired compounds per unit amount of rhodium, which is an expensive noble metal, is low. Therefore, these processes are not satisfactory from either the economical or the technical standpoint.

Various processes additionally using modified catalysts have been proposed in order to manufacture oxygen-containing compounds having two carbon atoms in high yield and with high selectivity. For instance, manganese, lithium, etc. were used as a co-catalyst in CA Patent No. 1,146,592 and Japanese Patent Public Disclosure (Laid-Open Publication) No. 8334/1981; lithium, magnesium and vanadium were used in Japanese Patent Public Disclosure (Laid-Open Publication) Nos. 62231/1982 and 109734/1982; scandium, yttrium and ytterbium were used in Japanese Patent Public Disclosure (Laid-Open Publication) No. 62233/1982; magnesium was used in U.S. Pat. No. 4,224,236; vanadium was used in Japanese Patent Public Disclosure (Laid-Open Publication) No. 62232/1982; and chromium was used in U.S. Pat. No. 4,327,190. In all of these processes, acetaldehyde and acetic acid are manufactured as main products, and the selectivity of ethanol is low.

Further, alcohol mixtures are produced by contacting synthesis gas with a catalyst containing copper, titanium, and at least one selected from the group consisting of chrome, manganese, cobalt, molybdenum, rhodium, platinum and iron, and an alkali or alkaline earth metal, (U.S. Pat. No. 4,459,369), or with an oxide complex catalyst containing copper, thorium, an alkali metal, etc., (U.S. Pat. No. 4,298,354), or with a catalyst comprising an iron group metal and rhodium, etc., (U.S. Pat. No. 4,537,909). In all of these processes, the selectivity of ethanol is also low.

Thus, no process has yet been made available which is capable of efficiently and economically manufacturing ethanol from a gas comprising carbon monoxide and hydrogen.

SUMMARY OF THE INVENTION

It is therefore an object of the present invention to provide a process for the manufacture of ethanol with high selectivity be reaction of carbon monoxide with hydrogen using a novel catalyst composition, said catalyst composition comprising (A) catalyst component consisting of
  (a) a rhodium component,
  (b) a lithium component, and
  (c) a component of at least one element selected from the group consisting of iridium, manganese, scandium, magesium, yttrium, ytterbium, lutecium, vanadium and chromium; and (B) catalyst component, which is supported on a separate carrier from said (A) catalyst component, being selected from the group consisting of
  (a) an iron component and a component of at least one element selected from the group consisting of iridium and palladium,
  (b) a molybdenum component and a component of at least one element selected from the group consisting of iridium and palladium,
  (c) an iron component, a molybdenum component and a component of at least one element selected from the group consisting of iridium and palladium, and
  (d) a copper component and optionally a component of at least one element selected from the group consisting of zinc and chromium.

Other objects and advantages of the present invention will become apparent to those skilled in the art from the following description and disclosure.

DETAILED DESCRIPTION OF THE PREFERRED EMBODIMENT

The present invention relates to a process for the manufacture of ethanol by reaction of carbon monoxide with hydrogen in the presence of a novel catalyst composition. The catalyst composition used in the present invention is composed essentially of the following catalyst components (A) and (B).

(A) A catalyst component containing rhodium, lithium and at least one element selected from the group consisting of iridium, manganese, scandium, magnesium, yttrium, ytterbium, lutecium, vanadium and chromium. [Hereinafter abbreviated as "the catalyst component (A)".]

(B) At least one catalyst component selected from a catalyst component (a) containing iron and/or molybdenum and at least one element selected from the group consisting of iridium and palladium and a catalyst component (b) containing copper and optionally at least one element selected from the group consisting of zinc and chromium. [Hereinafter abbreviated as "the catalyst component (B)".]

When only the catalyst component (A) is used, the main product is acetaldehyde, as seen in Table III which appears later, and the yield and selectivity of ethanol are low. When only the catalyst component (B) is used, the yield and selectivity of both acetaldehyde and ethanol are low and there is substantially no catalytic activity. On the other hand, when the catalyst component (A) and the catalyst component (B) are used in combination as in the present invention, the yield and selectivity of ethanol are increased significantly, and ethanol is manufactured efficiently as the main product.

Further, if catalyst components (A) and (B) are supported on the same carrier, the resulting catalyst composition has very low selectivity of ethanol (see Comparative Examples 17–22). Thus, according to the process of this invention, ethanol can be produced with a high carbon efficiency from a gaseous mixture of carbon oxide and hydrogen by using the aforesaid catalyst composition. This phenomenon was unexpected and is suprising. The reason for this has not yet been clarified.

The catalyst components (A) and (B) can be prepared separately. They can be used as a mixture or by packing the catalyst component (A) in the upper portion of a reactor and the catalyst component (B) in the lower portion.

In the preparation of the catalyst component (A) or (B), the above-mentioned catalyst elements are dispersed on a separate carrier as ordinarily done in the preparation of noble metal catalysts. The catalyst components used in the present invention can be prepared in accordance with an ordinary method used in the preparation of noble metal catalysts.

The catalyst components of the present invention can be prepared in accordance with, for example, an impregnation method, an immersion method, an ion exchange method, a co-precipitation method or a kneading method.

In the preparation of the catalyst component (A) or (B), the material compound used for rhodium or iridium can be a compound which is ordinarily used in the preparation of noble metal catalyst, such as a halide (e.g. a chloride or a bromide), an inorganic acid salt (e.g. a nitrate or a carbonate), an organic salt or a chelate compound (e.g. an acetate, an oxalate, an acetylacetonate salt or an ethylenediamine acetate), a carbonyl compound, an amine complex salt, a metal alkoxide or an alkyl metal compound. The material compound used for lithium, manganese, scandium, magnesium, yttrium, ytterbium, lutecium, vanadium or chromium can be a halide, an inorganic acid salt (e.g. a nitrate or a chlorate), a hydroxide, an organic acid salt (e.g. a formate or an acetate), a metal alkoxide compound, an alkyl metal compound or the like.

The material compound used for palladium can be a halide, a nitrate, a hydroxide, an organic acid salt (e.g. a formate or an acetate) or the like.

The material compound used for iron or molybdenum can be a halide, an inorganic acid salt (e.g. a halogen acid salt or a nitrate), an organic acid salt (e.g. a formate or an acetate), a carbonyl compound or the like.

The material compound used for copper or zinc can be halide, a halogen acid salt, a nitrate, a hydroxide, an organic acid salt (e.g. a formate, an acetate or an oxalate) or the like.

Of these compounds, a compound highly soluble in ethanol, water or any other appropriate solvent is preferred because the metal element contained in such a compound can easily be supported on a carrier.

The preparation of the catalyst component (A) or (B) will be explained below, focusing on the impregnation method.

A compound of each of the above-mentioned catalyst elements is dissolved in a single solvent such as water, methanol, ethanol, acetone, tetrahydrofuran, dioxane, n-hexane, benzene, toluene or the like, or in a solvent which is a mixture of any of these single solvents; to the resulting solution is added a carrier for impregnation with the solution; the solvent is removed by distillation; the residue is dried and, if necessary, subjected to a treatment such as heating, gas treatment or the like; the metal compound thereby being supported on the carrier.

With the catalyst component (A) or (B), the support on a carrier can be effected in accordance with various methods such as a method wherein all material compounds are dissolved together in a solvent and simultaneously supported on a carrier, a method wherein each material compound is sequentially supported on a carrier and a method wherein each material compound is sequentially supported on a carrier while being subjected, if necessary, to a treatment such as reduction, heat treatment or the like.

The catalyst component (A) or (B) can be prepared also by other methods such as an ion exchange method wherein metals are supported on a carrier by utilizing the ion exchangeability of the carrier, a coprecipitation method or a kneading method.

The catalyst components (A) and (B) prepared as above are ordinarily subjected to a reduction treatment for activation before they are used in reactions as a catalyst. The reduction is preferably conducted at an increased temperature using a hydrogen-containing gas, because this provides for a simple operation.

The reduction of the catalyst component (A) may be conducted at temperatures at which rhodium can be reduced, namely, at about 100° C. However, it is preferably conducted at temperatures between 200° C. and 600° C. This reduction by hydrogen may be conducted with the temperature being in-creased gradually or stepwise in order to attain thorough dispersion of each catalyst element. Alternatively, the reduction may be conducted using a reducing agent such as a combination of carbon monoxide and water, hydrazine, a boron hydride compound or an aluminium hydride compound.

The reduction of the catalyst compound (B) can be conducted in a method essentially the same as the one used for the catalyst component (A).

The carrier used in the present invention can be an ordinary carrier as long as it has a specific surface area of, preferably, 10 to 1,000 m2/g and a pore diameter of 10 Å or larger. Specific examples of the carrier include silica, a silicate, alumina, active carbon, an oxide of a metal (e.g. zirconium oxide, titanium oxide or magnesia), a molecular sieve, diatomaceous earth, etc. A silica type carrier is preferred.

The ratio of each constituent element in the catalyst component (A) is as follows.

The ratio of rhodium to carrier is 0.0001 to 0.5, preferably 0.001 to 0.3 by weight ratio, depending on the specific surface area of the carrier. The ratio of lithium to rhodium is 0.0001 to 3, preferably 0.001 to 2 by atomic ratio. The ratio of iridium to rhodium is 0.001 to 6, preferably 0.005 to 3 by atomic ratio. The ratio of manganese, scandium, magnesium, yttrium, ytterbium, lutecium, vanadium and chromium (hereinafter abbreviated as "other elements") to rhodium is 0.001 to 10, preferably 0.005 to 3 by atomic ratio.

The ratio of each constituent element in the catalyst component (B) is as follows.

The ratio of iridium to carrier is 0.0001 to 0.5, preferably 0.001 to 0.3 by weight ratio, depending on the specific surface area of the carrier. The ratio of iron to iridium is 0.001 to 10, preferably 0.05 to 5 by atomic ratio. The ratio of molybdenum to iridium is 0.001 to 10, preferably 0.05 to 5 by atomic ratio.

The ratio of palladium to carrier is 0.0001 to 0.5, preferably 0.001 to 0.3 by weight ratio, depending on the specific surface area of the carrier. The ratio of iron to palladium is 0.001 to 10, preferably 0.01 to 5 by atomic ratio. The ratio of molybdenum to palladium is 0.001 to 10, preferably 0.01 to 5 by atomic ratio.

The ratio of copper to carrier is 0.001 to 50, preferably 0.01 to 20 by weight ratio. The ratio of zinc to copper is 0.01 to 50, preferably 0.1 to 5 by atomic ratio. The ratio of chromium to copper is 0.01 to 50, preferably 0.1 to 5 by atomic ratio.

The present invention can be applied to, for example, a flow type fixed bed reactor. For instance, the catalyst component (B) is firstly placed in a reactor and then the catalyst component (A) is placed thereon, or, a mixture of the catalyst components (A) and (B) is placed in the reactor; subsequently, a material gas is introduced therein to induce a reaction, but in the former case, the material gas is first contacted with the catalyst component (A) and then with the catalyst component (B).

The products formed are separated and the unreacted portion of the material gas can be purified as necessary and reused.

The present invention can be applied also to a fluidized bed reactor. A material gas, the catalyst component (A) and the catalyst component (B) are mixed; then, the resulting mixture is introduced into a reactor and subjected to reaction. The present invention can be applied further to a liquid phase, non-uniform reaction wherein the catalyst components (A) and (B) are disposed together in a solvent and a material gas is fed therein to induce a reaction. The reaction conditions employed in the practice of the present invention are an appropriate combination of each reaction condition in order to manufacture oxygen-containing compounds composed essentially of ethanol in high yield and with high selectivity while minimizing the formation of hydrocarbons.

The reaction pressure can be atmospheric pressure, namely, 0 kg/cm² G, because the intended compounds can be manufactured in high yield and with high selectivity at that pressure. However, it can also be applied pressure in order to increase the space/time yield. Therefore, the reaction pressure can vary between 0 and 350 kg/cm² G, preferably 0 and 250 kg/cm² G. The reaction temperature is 150° to 450° C., preferably 180° to 350° C. When a high reaction temperature is used, the formation of hydrocarbons as byproducts increases and accordingly it becomes necessary for the feeding rate of a material gas to be increased or the ratio of carbon monoxide and hydrogen in the material gas to be altered. Hence, the space velocity [(feeding rate of a material gas)/(volume of catalyst)] is appropriately selected in the range between $10\ h^{-1}$ and $10^{-7}\ h^{-1}$ when expressed in normal state conditions (0° C. and 1 atm), depending on the reaction pressure, reaction temperature and material gas composition used.

The material gas mainly comprises carbon monoxide and hydrogen. It may further comprise gases such as nitrogen, argon, helium and methane and may furthermore comprise hydrocarbons, carbon dioxide, oxygen-containing compounds produced and water if they are in a gaseous state during reaction. The ratio of hydrogen to carbon monoxide is 0.1 to 10, preferably 0.2 to 5 by volume ratio. The proportion of carbon monoxide and hydrogen together in the material gas is 20 to 100% by volume, preferably 60 to 100% by volume. The present invention will be explained in more detail below by way of Examples. However, these Examples are shown in similar reaction conditions in order to make the present invention more understandable and the present invention is in no way restricted by them.

EXAMPLES (1) Outline of catalyst preparation procedure

A silica carrier of an amount shown in Table I was immersed in an aqueous or alcoholic solution containing metal salts also shown in Table I and was then dried at room temperature or under heating. The metal salts-containing carrier was packed in a Pyrex glass reaction tube and subjected to reduction under heating in a stream of hydrogencontaining gas, whereby each catalyst component (A) or (B) was prepared.

(2) Outline of reaction procedure

A catalyst component (B) of an amount shown in Table II was placed as a layer in titanium reaction tube with an inside diameter of 18 mm having a thermocouple-protecting tube with an outside diameter of 8 mm (apparatus I), or in a titanium reaction tube with an inside diameter of 14 mm having a thermocouple-protecting tube with an outside diameter of 6 mm (apparatus II). Subsequently, a catalyst component (A) of an amount as shown in Table II diluted with silica of an amount three times the catalyst component (A) was placed as a layer on the catalyst component (B) in the reaction tube. The inside of the reaction tube was purged with nitrogen and then the catalyst components (A) and (B) were subjected to re-reduction under heating at atmospheric pressure in a stream of a hydrogen-containing gas. Thereafter, a mixed gas consisting of predetermined proportions of hydrogen and carbon monoxide was fed into the reaction tube so that the mixed gas contacted first with the catalyst component (A) and then with the catalyst component (B) and a reaction was then carried out at a predetermined temperature and a predetermined pressure. Of the products formed, liquid products were captured by dissolving in water and gaseous products were collected directly and were subjected to gas chromatography so as to measure the amount of each product.

The results of reaction are shown in Table II.

In the Comparative Examples, the reaction was conducted in the same manner as above except that only the catalyst component (A) or (B), or said two components being supported on the same carrier, was used. The catalyst components used in Comparative Examples 17–22 in which said two components are supported on the same carrier are shown in Table I. The results of reaction are shown in Table III.

TABLE I

Preparation of Catalyst

| Ex. | Catalyst component (A) Metal salt (g) | | | | Carrier (ml) | Solvent | Catalyst component (B) Metal salt (g) | | | Carrier (ml) | Solvent |
|---|---|---|---|---|---|---|---|---|---|---|---|
| 1 | RhCl₃.3H₂O (0.480) | LiCl.H₂O (0.033) | MnCl₂.4H₂O (0.072) |  | 10 | C₂H₅OH | FeCl₂.4H₂O (0.109) | IrCl₄.H₂O (0.321) |  | 10 | C₂H₅OH |
| 2 | RhCl₃.3H₂O (1.20) | LiCl.H₂O (0.055) | ScCl₃.6H₂O (0.059) |  | 25 | H₂O | FeCl₃.6H₂O (0.370) | IrCl₄.H₂O (0.803) |  | 25 | H₂O |
| 3 | RhCl₃.3H₂O (1.20) | LiCl.H₂O (0.055) | MgCl₂.6H₂O (0.093) |  | " | C₂H₅OH | FeCl₃.6H₂O (0.370) | PdCl₂ (0.803) |  | " | " |
| 4 | RhCl₃.3H₂O (1.20) | LiCl.H₂O (0.055) | CrCl₃.6H₂O (0.122) |  | " | " | FeCl₃.6H₂O (0.370) | IrCl₄.H₂O (0.803) |  | " | " |
| 5 | RhCl₃.3H₂O (1.20) | LiCl.H₂O (0.055) | CrCl₃.6H₂O (0.122) |  | " | " | FeCl₃.6H₂O (0.370) | PdCl₂ (0.803) |  | " | " |
| 6 | RhCl₃.3H₂O (0.480) | LiCl.H₂O (0.011) | MnCl₂.4H₂O (0.018) | IrCl₄.H₂O (0.064) | 10 | " | FeCl₂.4H₂O (0.109) | IrCl₄.H₂O (0.321) |  | 10 | C₂H₅OH |
| 7 | RhCl₃.3H₂O (1.20) | LiCl.H₂O (0.022) | MnCl₂.4H₂O (0.018) | IrCl₄.H₂O (0.064) | " | " | FeCl₂.4H₂O (0.163) | PdCl₂ (0.266) |  | " | H₂O |
| 8 | RhCl₃.3H₂O (1.20) | LiCl.H₂O (0.055) | ScCl₃.6H₂O (0.059) | IrCl₄.H₂O (0.064) | 25 | H₂O | FeCl₃.6H₂O (0.370) | IrCl₄.H₂O (0.803) |  | 25 | " |
| 9 | RhCl₃.3H₂O (0.480) | LiCl.H₂O (0.033) | MnCl₂.4H₂O (0.012) |  | 10 | C₂H₅OH | MoCl₅ (0.035) | PdCl₂ (0.089) |  | 10 | C₂H₅OH |
| 10 | RhCl₃.3H₂O (1.20) | LiCl.H₂O (0.055) | ScCl₃.6H₂O (0.059) |  | 25 | H₂O | MoCl₅ (0.087) | IrCl₄.H₂O (0.803) |  | 25 | " |
| 11 | RhCl₃.3H₂O (1.20) | LiCl.H₂O (0.055) | ScCl₃.6H₂O (0.059) |  | " | " | MoCl₅ (0.087) | PdCl₂ (0.404) |  | " | " |
| 12 | RhCl₃.3H₂O (1.20) | LiCl.H₂O (0.055) | ScCl₃.6H₂O (0.059) |  | " | " | FeCl₃.6H₂O (0.218) | PdCl₂ (0.404) | MoCl₅ (0.052) | " | " |
| 13 | RhCl₃.3H₂O (1.20) | LiCl.H₂O (0.055) | YCl₃.6H₂O (0.138) |  | " | C₂H₅OH | MoCl₅ (0.087) | PdCl₂ (0.404) |  | " | " |
| 14 | RhCl₃.3H₂O (1.20) | LiCl.H₂O (0.055) | LuCl₃.6H₂O (0.178) |  | " | " | MoCl₅ (0.087) | PdCl₂ (0.404) |  | " | " |
| 15 | RhCl₃.3H₂O (1.20) | LiCl.H₂O (0.055) | VCl₃ (0.072) |  | " | " | MoCl₅ (0.087) | PdCl₂ (0.404) |  | " | " |
| 16 | RhCl₃.3H₂O (1.20) | LiCl.H₂O (0.055) | VCl₃ (0.072) | IrCl₄.H₂O (0.064) | " | H₂O | FeCl₃.6H₂O (0.218) | PdCl₂ (0.404) | MoCl₅ (0.052) | " | " |
| 17 | RhCl₃.3H₂O (1.20) | LiCl.H₂O (0.055) | ScCl₃.6H₂O (0.059) | IrCl₄.H₂O (0.064) | " | " | MoCl₅ (0.087) | PdCl₂ (0.404) |  | " | " |
| 18 | RhCl₃.3H₂O (1.20) | LiCl.H₂O (0.055) | ScCl₃.6H₂O (0.059) | IrCl₄.H₂O (0.064) | " | C₂H₅OH | FeCl₃.6H₂O (0.218) | PdCl₂ (0.404) | MoCl₅ (0.052) | " | " |
| 19 | RhCl₃.3H₂O (1.20) | LiCl.H₂O (0.055) | ScCl₃.6H₂O (0.059) | IrCl₄.H₂O (0.064) | " | " | MoCl₅ (0.087) | IrCl₄.H₂O (0.803) |  | " | " |
| 20 | RhCl₃.3H₂O (0.480) | LiCl.H₂O (0.033) | MnCl₂.4H₂O (0.011) |  | 10 | C₂H₅OH | FeCl₃.6H₂O (0.087) | PdCl₂ (0.404) |  | 10 | H₂O |
| 21 | RhCl₃.3H₂O (0.480) | LiCl.H₂O (0.033) | MnCl₂.4H₂O (0.011) |  | " | " | Cu(NO₃)₂.3H₂O (1.895) | Cr(NO₃)₃.9H₂O (1.460) |  | " | " |
| 22 | RhCl₃.3H₂O (1.20) | LiCl.H₂O (0.055) | ScCl₃.6H₂O (0.059) |  | 25 | " | Cu(NO₃)₂.3H₂O (1.895) | Cr(NO₃)₃.9H₂O (1.46) |  | " | " |
| 23 | RhCl₃.3H₂O (1.20) | LiCl.H₂O (0.055) | ScCl₃.6H₂O (0.059) |  | " | " | Cu(NO₃)₂.3H₂O (1.89) | Cr(NO₃)₃.9H₂O (1.46) |  | " | " |
| 24 | RhCl₃.3H₂O (1.20) | LiCl.H₂O (0.055) | ScCl₃.6H₂O (0.059) |  | " | " | Cu(NO₃)₂.3H₂O (1.89) | Zn(NO₃)₂.6H₂O (2.33) |  | " | " |
| 25 | RhCl₃.3H₂O (1.20) | LiCl.H₂O (0.055) | ScCl₃.6H₂O (0.059) |  | " | " | Cu(NO₃)₂.3H₂O (1.89) | Zn(NO₃)₂.6H₂O | Cr(NO₃)₃.9H₂O | " | " |

TABLE I-continued

| Comp. No. | | | | | | | | Carrier (ml) | Solvent |
|---|---|---|---|---|---|---|---|---|---|
| 26 | RhCl$_3$.3H$_2$O (1.20) | LiCl.H$_2$O (0.055) | YbCl$_3$.6H$_2$O (0.177) | | Cu(NO$_3$)$_2$.3H$_2$O (1.89) | Cr(NO$_3$)$_2$.9H$_2$O (2.33) | Cr(NO$_3$)$_3$.9H$_2$O (1.46) | " | " |
| 27 | RhCl$_3$.3H$_2$O (1.20) | LiCl.H$_2$O (0.055) | VCl$_3$ (0.072) | | Cu(NO$_3$)$_2$.3H$_2$O (1.89) | Zn(NO$_3$)$_2$.6H$_2$O (2.33) | Cr(NO$_3$)$_3$.9H$_2$O (1.46) | " | " |
| 28 | RhCl$_3$.3H$_2$O (1.20) | LiCl.H$_2$O (0.055) | CrCl$_3$.6H$_2$O (0.122) | | Cu(NO$_3$)$_2$.3H$_2$O (1.89) | Zn(NO$_3$)$_2$.6H$_2$O (2.33) | | " | " |
| 29 | RhCl$_3$.3H$_2$O (1.20) | LiCl.H$_2$O (0.055) | IrCl$_4$.H$_2$O (0.321) | MnCl$_2$.4H$_2$O (0.011) | Cu(NO$_3$)$_2$.3H$_2$O (1.89) | Zn(NO$_3$)$_2$.6H$_2$O (2.33) | | 10 | " |
| 30 | RhCl$_3$.3H$_2$O (0.480) | LiCl.H$_2$O (0.033) | IrCl$_4$.H$_2$O (0.064) | MnCl$_2$.4H$_2$O (0.011) | Cu(NO$_3$)$_2$.3H$_2$O (1.895) | Zn(NO$_3$)$_2$.6H$_2$O (2.333) | Cr(NO$_3$)$_3$.9H$_2$O (0.730) | " | " |
| 31 | RhCl$_3$.3H$_2$O (0.480) | LiCl.H$_2$O (0.033) | IrCl$_4$.H$_2$O (0.064) | ScCl$_3$.6H$_2$O (0.059) | Cu(NO$_3$)$_2$.3H$_2$O (1.895) | Zn(NO$_3$)$_2$.6H$_2$O (2.33) | Cr(NO$_3$)$_3$.9H$_2$O (1.46) | 25 | " |
| 32 | RhCl$_3$.3H$_2$O (1.20) | LiCl.H$_2$O (0.055) | IrCl$_4$.H$_2$O (0.064) | ScCl$_3$.6H$_2$O (0.059) | Cu(NO$_3$)$_2$.3H$_2$O (1.89) | Zn(NO$_3$)$_2$.6H$_2$O (2.33) | Cr(NO$_3$)$_3$.9H$_2$O (1.46) | " | " |
| 33 | RhCl$_3$.3H$_2$O (1.20) | LiCl.H$_2$O (0.055) | IrCl$_4$.H$_2$O (0.064) | YbCl$_3$.6H$_2$O (0.177) | Cu(NO$_3$)$_2$.3H$_2$O (1.89) | Zn(NO$_3$)$_2$.6H$_2$O (2.33) | Cr(NO$_3$)$_3$.9H$_2$O (1.46) | " | " |
| 34 | RhCl$_3$.3H$_2$O (1.20) | LiCl.H$_2$O (0.055) | IrCl$_4$.H$_2$O (0.064) | LuCl$_3$.6H$_2$O (0.178) | Cu(NO$_3$)$_2$.3H$_2$O (1.89) | Zn(NO$_3$)$_2$.6H$_2$O (2.33) | Cr(NO$_3$)$_3$.9H$_2$O (1.46) | " | " |
| 35 | RhCl$_3$.3H$_2$O (1.20) | LiCl.H$_2$O (0.055) | IrCl$_4$.H$_2$O (0.064) | CrCl$_3$.6H$_2$O (0.122) | Cu(NO$_3$)$_2$.3H$_2$O (1.89) | Zn(NO$_3$)$_2$.6H$_2$O (2.33) | Cr(NO$_3$)$_3$.9H$_2$O (1.46) | " | " |

| Comp. No. | Catalyst Component | | | Metal salt (g) | | | Carrier (ml) | Solvent |
|---|---|---|---|---|---|---|---|---|
| 17 | RhCl$_3$.3H$_2$O (0.192) | LiCl.H$_2$O (0.0088) | MgCl$_2$.6H$_2$O (0.0149) | FeCl$_3$.6H$_2$O (0.0148) | Cu(NO$_3$)$_2$.3H$_2$O (0.379) | PdCl$_2$ (0.0321) | 4 | C$_2$H$_5$OH |
| 18 | RhCl$_3$.3H$_2$O (0.288) | LiCl.H$_2$O (0.0198) | MnCl$_2$.4H$_2$O (0.0072) | MoCl$_5$ (0.007) | | PdCl$_2$ (0.0178) | 6 | H$_2$O |
| 19 | RhCl$_3$.3H$_2$O (0.192) | LiCl.H$_2$O (0.0088) | VCl$_3$ (0.0115) | MoCl$_5$ (0.0035) | | PdCl$_2$ (0.0162) | 4 | C$_2$H$_5$OH |
| 20 | RhCl$_3$.3H$_2$O (0.096) | LiCl.H$_2$O (0.0066) | MnCl$_2$.4H$_2$O (0.0022) | Cu(NO$_3$)$_2$.3H$_2$O (0.379) | | | 2 | C$_2$H$_5$OH |
| 21 | RhCl$_3$.3H$_2$O (0.096) | LiCl.H$_2$O (0.0066) | MnCl$_2$.4H$_2$O (0.0022) | Cu(NO$_3$)$_2$.3H$_2$O (0.379) | Cr(NO$_3$)$_3$.9H$_2$O | | 2 | C$_2$H$_5$OH |
| 22 | RhCl$_3$.3H$_2$O (0.480) | LiCl.H$_2$O (0.0220) | ScCl$_3$.6H$_2$O (0.0236) | Cu(NO$_3$)$_2$.3H$_2$O (1.89) | Zn(NO$_3$)$_2$.3H$_2$O (2.33) | | 10 | CH$_3$OH |

EXAMPLE 1

Catalyst component (A): A silica gel (DAVISON #57 having a specific surface area of about 300 m²/g) subjected in advance to calcination and degassing at about 300° C. for about 2 hours under high vacuum (about 1 mmHg) was immersed in about 6 ml of an ethanol solution containing the metal salts specified in Table I. Then, ethanol was distilled off using a rotary evaporator and the residue was dried at room temperature for about 15 minutes under high vacuum (about 1 mmHg). This dried matter was placed in a Pyrex glass reaction tube and subjected to reduction at 400° C. for 4 hours at atmospheric pressure in a stream of a mixed gas consisting of hydrogen and nitrogen ($H_2$: 60 ml/min, $N_2$: 60 ml/min), whereby a Rh-Li-Mn catalyst component was prepared.

Catalyst component (B): The same procedure as for the catalyst component (A) was conducted except that the metal salts specified in Table I were used, whereby a Fe-Ir catalyst component was prepared.

EXAMPLE 2

Catalyst component (A): The metal salts specified in Table I were dissolved in 11.5 ml of water, and thereto was added a silica gel (DAVISON #57). The mixture was subjected to drying at room temperature for 1 hour and then at about 60° C. for about 18 hours. The dried matter was placed in a Pyrex glass reaction tube and subjected to reduction at 400° C. for 5 hours in a stream of hydrogen (180 ml/min), whereby a Rh-Li-Sc catalyst component was prepared.

Catalyst component (B): The same procedure as for the catalyst component (A) was conducted except that the metal salts specified in Table I were used, whereby a Fe-Ir catalyst component was prepared.

EXAMPLE 3

Catalyst component (A): The metal salts specified in Table I were dissolved in 30 ml of ethanol, and thereto was added a silica gel. Then, ethanol was distilled off using a rotary evaporator. The subsequent procedure was the same as in Example 2, whereby a Rh-Li-Mg catalyst component was prepared.

Catalyst component (B): The same procedure as in Example 2 was followed except that the metal salts specified in Table I were dissolved in 30 ml of water acidified (pH about 1) with hydrochloric acid, whereby a Fe-Pd catalyst component was prepared.

EXAMPLE 4

Catalyst component (A): The same procedure as in Example 3 was followed except that the metal salts specified in Table I were used, whereby a Rh-Li-Cr catalyst component was prepared.

Catalyst component (B): The same procedure and composition as in Example 2 were used, whereby a Fe-Ir catalyst component was prepared.

EXAMPLE 5

Catalyst component (A): The same procedure and composition as in Example 4 were used, whereby a Rh-Li-Cr catalyst component was prepared.

Catalyst component (B): The same procedure and composition as in Example 3 were used, whereby a Fe-Pd catalyst component was prepared.

EXAMPLE 6

Catalyst component (A): The same procedure as in Example 1 was followed except that the metal salts specified in Table I were used, whereby a Rh-Li-Ir-Mn catalyst component was prepared.

Catalyst component (B): The same procedure and composition as in Example 1 were used, whereby a Fe-Ir catalyst component was prepared.

EXAMPLE 7

Catalyst component (A): The same procedure as in Example 1 was followed except that the metal salts specified in Table I were used, whereby a Rh-Li-Ir-Mn catalyst component was prepared.

Catalyst component (B): The same procedure as in Example 1 was followed except that the metal salts and solvent specified in Table I were used, whereby a Fe-Pd catalyst component was prepared.

EXAMPLE 8

Catalyst component (A): The same procedure as in Example 2 was followed except that the metal salts specified in Table I were used, whereby a Rh-Li-Ir-Sc catalyst component was prepared.

Catalyst component (B): The same procedure and composition as in Example 2 were used, whereby a Fe-Ir catalyst component was prepared.

EXAMPLE 9

Catalyst component (A): The same procedure as in Example 1 was followed except that the metal salts specified in Table I were used, whereby a Rh-Li-Mn catalyst component was prepared.

Catalyst component (B): The same procedure as in Example 1 was followed except that the metal salts and solvent specified in Table I were used, whereby a Mo-Pd catalyst component was prepared.

EXAMPLE 10

Catalyst component (A): The same procedure and composition as in Example 2 were used, whereby a Rh-Li-Sc catalyst component was prepared.

Catalyst component (B): The metal salts specified in Table I were dissolved in 30 ml of ethanol, and thereto was added a silica gel. Then, ethanol was distilled off using a rotary evaporator. The subsequent procedure was conducted in the same manner as in Example 2, whereby a Mo-Ir catalyst component was prepared.

EXAMPLE 11

Catalyst component (A): The same procedure and composition as in Example 2 were used, whereby a Rh-Li-Sc catalyst component was prepared.

Catalyst component (B): The same procedure as in Example 10 was followed except that the metal salts specified in Table I were used, whereby a Mo-Pd catalyst component was prepared.

EXAMPLE 12

Catalyst component (A): The same procedure and composition as in Example 2 were used, whereby a Rh-Li-Sc catalyst component was prepared.

Catalyst component (B): The same procedure as in Example 10 was followed except that the metal salts specified in Table I were used, whereby a Fe-Mo-Pd catalyst component was prepared.

EXAMPLE 13

Catalyst component (A): The same procedure as in Example 3 was followed except that the metal salts specified in Table I were used, whereby a Rh-Li-Y catalyst component was prepared.

Catalyst component (B): The same procedure and composition as in Example 11 were used, whereby a Mo-Pd catalyst component was prepared.

EXAMPLE 14

Catalyst component (A): The same procedure as in Example 3 was followed except that the metal salts specified in Table I were used, whereby a Rh-Li-Lu catalyst component was prepared.

Catalyst component (B): The same procedure and composition as in Example 11 were used, whereby a Mo-Pd catalyst component was prepared.

EXAMPLE 15

Catalyst component (A): The same procedure as in Example 3 was followed except that the metal salts specified in Table I were used, whereby a Rh-Li-V catalyst component was prepared.

Catalyst component (B): The same procedure and composition as in Example 11 were used, whereby a Mo-Pd catalyst component was prepared.

EXAMPLE 16

Catalyst component (A): The same procedure as in Example 3 was followed except that the metal salts specified in Table I were used, whereby a Rh-Li-Ir-V catalyst component was prepared.

Catalyst component (B): The same procedure and composition as in Example 12 were used, whereby a Fe-Mo-Pd catalyst component was prepared.

EXAMPLE 17

Catalyst component (A): The same procedure and composition as in Example 8 were used, whereby a Rh-Li-Ir-Sc catalyst component was prepared.

Catalyst component (B): The same procedure and composition as in Example 11 were used, whereby a Mo-Pd catalyst component was prepared.

EXAMPLE 18

Catalyst component (A): The same procedure and composition as in Example 8 were used, whereby a Rh-Li-Ir-Sc catalyst component was prepared.

Catalyst component (B): The same procedure and composition as in Example 12 were used, whereby a Fe-Mo-Pd catalyst component was prepared.

EXAMPLE 19

Catalyst component (A): The same procedure and composition as in Example 8 were used, whereby a Rh-Li-Ir-Sc catalyst component was prepared.

Catalyst component (B): The same procedure and composition as in Example 10 were used, whereby a Mo-Ir catalyst component was prepared.

EXAMPLE 20

Catalyst component (A): The same procedure as in Example 1 was followed except that the metal salts specified in Table I were used, whereby a Rh-Li-Mn catalyst component was prepared.

Catalyst component (B): The same procedure as in Example 7 was followed except that the metal salts specified in Table I were used, whereby a Cu catalyst component was prepared.

EXAMPLE 21

Catalyst component (A): The same procedure and composition as in Example 20 were used, whereby a Rh-Li-Mn catalyst component was prepared.

Catalyst component (B): The same procedure as in Example 7 was followed except that the metal salts specified in Table I were used, whereby a Cu-Cr catalyst component was prepared.

EXAMPLE 22

Catalyst component (A): The metal salts specified in Table I were dissolved in 11.5 ml of methanol, and thereto was added a silica gel (Fuji-DAVISON Gr-91112 having a specific surface area of 268 $m^2/g$). The mixture was dried at room temperature for 15 hours under vacuum (about 30 mmHg). The dried matter was packed in a Pyrex glass reaction tube and subjected to reduction at 450° C. for 5 hours in a hydrogen stream (40 ml/min), whereby a Rh-Li-Sc catalyst component was prepared.

Catalyst component (B): The metal salts specified in Table I were dissolved in 5 ml of water, and thereto was added a silica gel (DAVISON #57). The mixture was dried at about 30° C. for about 5 hours under vacuum (about 30 mmHg). The subsequent procedure was the same as for the catalyst component (A) except that the reduction temperature was 400° C., whereby a Cu catalyst component was prepared.

EXAMPLE 23

Catalyst component (A): The same procedure and composition as in Example 22 were used, whereby a Rh-Li-Sc catalyst component was prepared.

Catalyst component (B): The same procedure as in Example 22 was followed except that the metal salts specified in Table I were used, whereby a Cu-Cr catalyst component was prepared.

EXAMPLE 24

Catalyst component (A): The same procedure and composition as in Example 22 were used, whereby a Rh-Li-Sc catalyst component was prepared.

Catalyst component (B): The same procedure as in Example 22 was followed except that the metal salts specified in Table I were used, whereby a Cu-Zn catalyst component was prepared.

EXAMPLE 25

Catalyst component (A): The same procedure and composition as in Example 22 were used, whereby a Rh-Li-Sc catalyst component was prepared.

Catalyst component (B): The same procedure as in Example 22 was followed except that the metal salts specified in Table I were dissolved in 10 ml of water, whereby a Cu-Zn-Cr catalyst component was prepared.

EXAMPLE 26

Catalyst component (A): The metal salts specified in Table I were dissolved in 30 ml of ethanol, and thereto was added a silica gel (Fuji-DAVISON having a specific surface area of 260 $m^2/g$). The mixture was dried at about 30° C. for 5 hours under vacuum (about 30 mmHg). Thus, the dried matter was subjected to reduction in the same manner as in Example 2, whereby a Rh-Li-Yb catalyst component was prepared.

Catalyst component (B): The same procedure and composition as in Example 23 were used, whereby a Cu-Cr catalyst component was prepared.

EXAMPLE 27

Catalyst component (A): The same procedure as in Example 26 was followed except that the metal salts specified in Table I were used, whereby a Rh-Li-V catalyst component was prepared.

Catalyst component (B): The same procedure and composition as in Example 25 were used, whereby a Cu-Zn-Cr catalyst component was prepared.

EXAMPLE 28

Catalyst component (A): The same procedure as in Example 26 was followed except that the metal salts specified in Table I were used, whereby a Rh-Li-Cr catalyst component was prepared.

Catalyst component (B): The same procedure and composition as in Example 22 were used, whereby a Cu catalyst component was prepared.

EXAMPLE 29

Catalyst component (A): The same procedure as in Example 1 was followed except that the metal salts specified in Table I were used, whereby a Rh-Li-Ir-Mn catalyst component was prepared.

Catalyst component (B): The same procedure as in Example 7 was followed except that the metal salts specified in Table I were used, whereby a Cu catalyst component was prepared.

EXAMPLE 30

Catalyst component (A): The same procedure as in Example 1 was followed except that the metal salts specified in Table I were used, whereby a Rh-Li-Ir-Mn catalyst component was prepared.

Catalyst component (B): The same procedure as in Example 7 was followed except that the metal salts specified in Table I were used, whereby a Cu-Zn-Cr catalyst component was prepared.

EXAMPLE 31

Catalyst component (A): The same procedure as in Example 22 was followed except that the metal salts specified in Table I were used, whereby a Rh-Li-Ir-Sc catalyst component was prepared.

Catalyst component (B): The same procedure as in Example 22 was followed except that the metal salts specified in Table I were used, whereby a Cu-Zn catalyst component was prepared.

EXAMPLE 32

Catalyst component (A): The same procedure and composition as in Example 31 were used, whereby a Rh-Li-Ir-Sc catalyst component was prepared.

Catalyst component (B): The same procedure and composition as in Example 25 were used, whereby a Cu-Zn-Cr catalyst component was prepared.

EXAMPLE 33

Catalyst component (A): The same procedure as in Example 26 was followed except that the metal salts specified in Table I were used, whereby a Rh-Li-Ir-Yb catalyst component was prepared.

Catalyst component (B): The same procedure and composition as in Example 25 were used, whereby a Cu-Zn-Cr catalyst component was prepared.

EXAMPLE 34

Catalyst component (A): The same procedure as in Example 26 was followed except that the metal salts specified in Table I were used, whereby a Rh-Li-Ir-Lu catalyst component was prepared.

Catalyst component (B): The same procedure and composition as in Example 24 were used, whereby a Cu-Zn catalyst component was prepared.

EXAMPLE 35

Catalyst component (A): The same procedure as in Example 26 was followed except that the metal salts specified in Table I were used, whereby a Rh-Li-Ir-Cr catalyst component was prepared.

Catalyst component (B): The same procedure and composition as in Example 25 were used, whereby a Cu-Zn-Cr catalyst component was prepared.

COMPARATIVE EXAMPLE 1

The same procedure and composition as in the catalyst component (A) of Example 20 were used, whereby a Rh-Li-Mn catalyst component was prepared.

COMPARATIVE EXAMPLE 2

The same procedure and composition as in the catalyst component (A) of Example 11 were used, whereby a Rh-Li-Sc catalyst component was prepared.

COMPARATIVE EXAMPLE 3

The same procedure and composition as in the catalyst component (A) of Example 3 were used, whereby a Rh-Li-Mg catalyst component was prepared.

COMPARATIVE EXAMPLE 4

The same procedure and composition as in the catalyst component (A) of Example 13 were used, whereby a Rh-Li-Y catalyst component was prepared.

COMPARATIVE EXAMPLE 5

The same procedure and composition as in the catalyst component (A) of Example 26 were used, whereby a Rh-Li-Yb catalyst component was prepared.

COMPARATIVE EXAMPLE 6

The same procedure and composition as in the catalyst component (A) of Example 14 were used, whereby a Rh-Li-Lu catalyst component was prepared.

COMPARATIVE EXAMPLE 7

The same procedure and composition as in the catalyst component (A) of Example 15 were used, whereby a Rh-Li-V catalyst component was prepared.

COMPARATIVE EXAMPLE 8

The same procedure and composition as in the catalyst component (A) of Example 4 were used, whereby a Rh-Li-Cr catalyst component was prepared.

COMPARATIVE EXAMPLE 9

The same procedure and composition as in the catalyst component (B) of Example 1 were used, whereby a Fe-Ir catalyst component was prepared.

COMPARATIVE EXAMPLE 10

The same procedure and composition as in the catalyst component (B) of Example 3 were used, whereby a Fe-Pd catalyst component was prepared.

COMPARATIVE EXAMPLE 11

The same procedure and composition as in the catalyst component (B) of Example 9 were used, whereby a Mo-Pd catalyst component was prepared.

COMPARATIVE EXAMPLE 12

The same procedure and composition as in the catalyst component (B) of Example 10 were used, whereby a Mo-Ir catalyst component was prepared.

COMPARATIVE EXAMPLE 13

The same procedure and composition as in the catalyst component (B) of Example 12 were used, whereby a Fe-Mo-Pd catalyst component was prepared.

COMPARATIVE EXAMPLE 14

The same procedure and composition as in the catalyst component (B) of Example 20 were used, whereby a Cu catalyst component was prepared.

COMPARATIVE EXAMPLE 15

The same procedure and composition as in the catalyst component (B) of Example 21 were used, whereby a Cu-Cr catalyst component was prepared.

COMPARATIVE EXAMPLE 16

The same procedure and composition as in the catalyst component (B) of Example 24 were used, whereby a Cu-Zn catalyst component was prepared.

COMPARATIVE EXAMPLE 17

The same procedure as in Example 3 was conducted except that the metal salts specified in Table I and ethanol (as a solvent) were used, whereby a Rh-Li-Mg-Fe-Pd catalyst component was prepared.

COMPARATIVE EXAMPLE 18

The same procedure as in Example 9 was conducted except that the metal salts specified in Table I and water (as a solvent) were used, whereby a Rh-Li-Mn-Mo-Pd catalyst component was prepared.

COMPARATIVE EXAMPLE 19

The same procedure as in Example 15 was conducted except that the metal salts specified in Table I and ethanol (as a solvent) were used, whereby a Rh-Li-V-Mo-Pd catalyst component was prepared.

COMPARATIVE EXAMPLE 20

The same procedure as in Example 20 was conducted except that the metal salts specified in Table I and ethanol (as a solvent) were used, whereby a Rh-Li-Mn-Cu catalyst component was prepared.

COMPARATIVE EXAMPLE 21

The same procedure as in Example 21 was conducted except that the metal salts specified in Table I and ethanol (as a solvent) were used, whereby a Rh-Li-Mn-Cu-Cr catalyst component was prepared.

COMPARATIVE EXAMPLE 22

The same procedure as in Example 24 was conducted except that the metal salts specified in Table I and methanol (as a solvent) were used, whereby a Rh-Li-Sc-Cu-Zn catalyst component was prepared.

TABLE II

| | Catalyst component (a) | | Catalyst component (B) | | | Reaction pressure (kg/cm$^2$) | Reaction temperature (°C.) | Gas flow rate (Nl/hr) | H$_2$/CO (V/V) | Results of Reaction | | | | |
|---|---|---|---|---|---|---|---|---|---|---|---|---|---|---|
| | | | | | | | | | | CO conversion (%) | Selectivity (%) | | | |
| Ex. | Catalyst | Amount used (ml) | Catalyst | Amount used (ml) | Reaction apparatus | | | | | | EtOH | AcH | AcOH | CH$_4$ |
| 1 | Rh—Li—Mn | 6 | Fe—Ir | 2 | I | 30 | 292 | 210 | 2 | 3.7 | 54.6 | 14.2 | 5.0 | 21.6 |
| 2 | Rh—Li—Sc | 10 | " | 2.5 | " | " | 285 | " | 2.5 | 6.2 | 50.1 | 9.9 | 3.5 | 29.2 |
| 3 | Rh—Li—Mg | 4 | Fe—Pd | 1 | II | 20 | 275 | 36 | 2 | 8.1 | 46.1 | 4.3 | 5.0 | 24.0 |
| 4 | Rh—Li—Cr | " | Fe—Ir | " | " | " | " | " | " | 4.2 | 49.4 | 6.9 | 5.6 | 27.4 |
| 5 | " | " | Fe—Pd | " | " | " | " | " | " | 4.1 | 53.1 | 2.9 | 4.0 | 27.6 |
| 6 | Rh—Li—Ir—Mn | 7 | Fe—Ir | 3 | I | 33 | 290 | 210 | 3.3 | 9.1 | 61.3 | 5.4 | 1.2 | 28.4 |
| 7 | " | " | Fe—Pd | " | " | 30 | 285 | " | 2.5 | 6.5 | 58.3 | 7.0 | 2.7 | 24.3 |
| 8 | Rh—Li—Ir—Sc | 10 | Fe—Ir | 2.5 | " | " | " | " | " | 5.3 | 53.0 | 10.1 | 2.5 | 27.7 |
| 9 | Rh—Li—Mn | 6 | Mo—Pd | 2 | " | " | 291 | " | " | 4.7 | 60.9 | 4.5 | 1.6 | 27.3 |
| 10 | Rh—Li—Sc | 10 | Mo—Ir | 2.5 | " | " | 285 | " | " | 6.3 | 50.0 | 5.3 | 2.7 | 30.8 |
| 11 | " | " | Mo—Pd | " | " | " | " | " | " | 6.1 | 55.3 | 4.1 | 2.6 | 29.3 |
| 12 | " | " | Fe—Mo—Pd | " | " | " | " | " | " | 6.2 | 56.4 | 3.6 | 2.6 | 29.0 |
| 13 | Rh—Li—Y | 4 | Mo—Pd | 1 | II | 20 | 275 | 36 | 2 | 8.2 | 47.2 | 2.1 | 5.4 | 25.4 |
| 14 | Rh—Li—Lu | " | " | " | " | " | " | " | " | 9.0 | 50.5 | 1.1 | 4.7 | 27.9 |
| 15 | Rh—Li—V | " | " | " | " | " | " | " | " | 5.9 | 48.9 | 2.4 | 3.4 | 27.8 |
| 16 | Rh—Li—Ir—V | " | Fe—Mo—Pd | " | " | " | " | " | " | 5.0 | 52.2 | 1.3 | 5.6 | 27.4 |
| 17 | Rh—Li—Ir—Sc | 10 | Mo—Pd | 2.5 | I | 30 | 285 | 210 | 2.5 | " | 57.2 | 4.0 | 2.1 | 28.9 |
| 18 | " | " | Fe—Mo—Pd | " | " | " | " | " | " | 5.1 | 58.3 | 3.0 | 2.2 | 29.0 |
| 19 | " | " | Mo—Ir | " | " | " | " | " | " | 5.4 | 53.1 | 5.6 | 2.5 | 29.8 |
| 20 | Rh—Li—Mn | 2 | Cu | 2 | II | 20 | 283 | 40 | " | 5.3 | 61.3 | 1.2 | 5.6 | 24.2 |
| 21 | " | " | Cu—Cr | " | " | " | 280 | " | " | 5.1 | 62.0 | 1.1 | 7.0 | 23.8 |
| 22 | Rh—Li—Sc | 10 | Cu | 10 | I | " | 275 | 210 | 2 | 4.7 | 62.0 | 1.7 | 2.8 | 27.8 |
| 23 | " | " | Cu—Cr | " | " | " | " | " | " | 4.8 | 64.0 | 2.0 | 1.2 | 28.2 |
| 24 | " | " | Cu—Zn | " | " | " | " | " | " | " | 64.3 | 1.6 | 1.4 | 28.0 |
| 25 | " | " | Cu—Zn—Cr | " | I | " | " | " | " | " | 64.9 | 1.1 | 1.5 | 27.5 |
| 26 | Rh—Li—Yb | 4 | Cu—Cr | 4 | II | " | " | 36 | " | 9.9 | 47.9 | 0.6 | 7.1 | 26.0 |
| 27 | Rh—Li—V | " | Cu—Zn—Cr | " | " | " | " | " | " | 6.0 | 51.0 | 0.9 | 5.4 | 28.3 |
| 28 | Rh—Li—Cr | " | Cu | " | " | " | " | " | " | 4.0 | 51.1 | 1.7 | 7.1 | 27.9 |
| 29 | Rh—Li—Ir—Mn | 2 | " | 2 | " | " | 285 | 40 | 2.5 | 5.7 | 62.5 | 1.2 | 6.4 | 23.7 |
| 30 | " | " | Cu—Zn—Cr | " | " | " | 283 | " | " | 5.4• | 63.9 | 1.1 | 4.8 | 23.1 |
| 31 | Rh—Li—Ir—Sc | 10 | Cu—Zn | 10 | I | " | 275 | 210 | 2 | 3.6 | 67.4 | 1.7 | 1.4 | 23.9 |
| 32 | " | " | Cu—Zn—Cr | " | " | " | " | " | " | " | 67.9 | 1.3 | 1.5 | 23.7 |

TABLE II-continued

| | Catalyst component (a) | | Catalyst component (B) | | Results of Reaction | | | | | | Selectivity (%) | | | |
|---|---|---|---|---|---|---|---|---|---|---|---|---|---|---|
| Ex. | Catalyst | Amount used (ml) | Catalyst | Amount used (ml) | Reaction apparatus | Reaction pressure (kg/cm$^2$) | Reaction temperature (°C.) | Gas flow rate (Nl/hr) | H$_2$/CO (V/V) | CO conversion (%) | EtOH | AcH | AcOH | CH$_4$ |
| 33 | Rh—Li—Ir—Yb | 4 | " | 4 | II | " | " | 36 | " | 7.4 | 51.9 | 1.3 | 6.9 | 22.2 |
| 34 | Rh—Li—Ir—Lu | " | Cu—Zn | " | " | " | " | " | " | 6.8 | 55.0 | 1.3 | 8.1 | 24.2 |
| 35 | Rh—Li—Ir—Cr | " | Cu—Zn—Cr | " | " | " | " | " | " | 3.0 | 61.1 | 0.7 | 7.0 | 23.8 |

TABLE III

| Comp. Ex. | Catalyst component (A) | | Catalyst component (B) | | Reaction apparatus | Reaction pressure (kg/cm$^2$) | Reaction temperature (°C.) | Gas flow rate (Nl/hr) | H$_2$/CO (V/V) | CO conversion (%) | Selectivity (%) | | | |
|---|---|---|---|---|---|---|---|---|---|---|---|---|---|---|
| | Catalyst | Amount used (ml) | Catalyst | Amount used (ml) | | | | | | | EtOH | AcH | AcOH | CH$_4$ |
| 1 | Rh—Li—Mn | 2 | — | | II | 20 | 280 | 40 | 2.5 | 5.2 | 15.1 | 50.5 | 7.4 | 23.0 |
| 2 | Rh—Li—Sc | 10 | — | | I | 30 | 285 | 210 | " | 6.0 | 18.9 | 41.9 | 5.2 | 28.8 |
| 3 | Rh—Li—Mg | 4 | — | | II | 20 | 275 | 36 | 2 | 7.9 | 6.9 | 44.3 | 10.8 | 23.5 |
| 4 | Rh—Li—Y | " | — | | " | " | " | " | " | 8.0 | 9.3 | 39.5 | " | 24.8 |
| 5 | Rh—Li—Yb | " | — | | " | " | " | " | " | 9.7 | 7.6 | 40.9 | 8.4 | 25.6 |
| 6 | Rh—Li—Lu | " | — | | " | " | " | " | " | 8.8 | 9.1 | 43.0 | 9.6 | 27.2 |
| 7 | Rh—Li—V | " | — | | " | " | " | " | " | 5.8 | 16.6 | 35.3 | 6.8 | " |
| 8 | Rh—Li—Cr | " | — | | " | " | " | " | " | 3.9 | 13.4 | 43.6 | 8.8 | 27.3 |
| 9 | — | | Fe—Ir | 2 | " | 30 | 290 | 40 | 3 | 2.1 | 4.3 | 0.0 | 0.1 | 26.3 |
| 10 | — | | Fe—Pd | " | " | " | 281 | " | " | 0.8 | 0.0 | " | 0.0 | 0.0 |
| 11 | — | | Mo—Pd | " | " | " | 295 | " | 2 | 2.3 | 1.5 | " | " | 14.9 |
| 12 | — | | Mo—Ir | " | " | " | 270 | " | 3 | 3.2 | 7.6 | " | 0.7 | 32.6 |
| 13 | — | | Fe—Mo—Pd | " | " | " | 295 | " | " | 1.7 | 2.1 | " | 0.0 | 20.4 |
| 14 | — | | Cu | " | " | 20 | 280 | " | 2.5 | 0.1 | 0.0 | " | " | 0.0 |
| 15 | — | | Cu—Cr | " | " | " | " | " | " | 0.2 | " | " | " | " |
| 16 | — | | Cu—Zn | " | " | " | 281 | " | " | 0.1 | " | " | " | " |
| | Catalyst Component | | | | | | | | | | | | | |
| | Catalyst | Amount used (ml) | | | | | | | | | | | | |
| 17 | Rh—Li—Mg—Fe—Pd | 4 | | | II | 20 | 275 | 36 | 2 | 2.4 | 24.0 | 19.6 | 2.8 | 47.4 |
| 18 | Rh—Li—Mn—Mo—Pd | 6 | | | I | 30 | 291 | 210 | 2.5 | 0.6 | 7.1 | 5.1 | 3.7 | 39.2 |
| 19 | Rh—Li—V—Mo—Pd | 4 | | | II | 20 | 275 | 36 | 2 | 6.6 | 21.3 | 8.7 | 3.6 | 30.1 |
| 20 | Rh—Li—Mn—Cu | 2 | | | II | 20 | 283 | 40 | 2.5 | 0.2 | 33.9 | 5.2 | 3.1 | 25.0 |
| 21 | Rh—Li—Mn—Cu—Cr | 2 | | | II | 20 | 280 | 40 | 2.5 | 0.2 | 35.3 | 6.3 | 2.9 | 29.8 |
| 22 | Rh—Li—Sc—Cu—Zn | 10 | | | I | 20 | 275 | 210 | 2 | 0.0 | 0.0 | 0.0 | 0.0 | 0.0 |

Note:

Co conversion = $\frac{\text{Moles of carbon monoxide consumed}}{\text{Moles of carbon monoxide fed}} \times 100$ Selectivity (%) is based on carbon monoxide consumed.

EtOH: Total ethanol formed including ethanol derived from ethyl acetate.

AcH: Acetaldehyde.

AcOH: Total acetic acid formed including acetic acid derived from acetic acid esters.

CH$_4$: Methane.

In Table IV are also shown the comparisons of Comparative Examples 17-22 with the corresponding Examples 3, 9, 15, 20, 21, 24, respectively, with respect to the selectivity of ethanol.

TABLE IV

| | Selectivity of EtOH |
|---|---|
| Ex. 3 | 46.1 |
| Comp. Ex. 17 | 24.0 |
| Ex. 9 | 60.9 |
| Comp. Ex. 18 | 7.1 |
| Ex. 15 | 48.9 |
| Comp. Ex. 19 | 21.3 |
| Ex. 20 | 61.3 |
| Comp. Ex. 20 | 33.9 |
| Ex. 21 | 62.0 |
| Comp. Ex. 21 | 35.3 |
| Ex. 24 | 64.3 |
| Comp. Ex. 22 | 0.0 |

As is obvious from the above results, Examples in which the catalyst components (A) and (B) are supported on the separate carrier are remarkably superior to the corresponding Comparative Examples in which catalytic components (A) and (B) are supported on the same carrier with respect to the selectivity of ethanol.

What is claimed as new and desired to be secured by Letters Patent of the United States is:

1. In a process for the manufacture of ethanol by contacting a gas comprising carbon monoxide and hydrogen with a catalyst composition, the improvement wherein said catalyst composition consists essentially of the following two groups of catalyst components, (A) catalyst component, supported on a carrier consisting of
  (a) a rhodium component,
  (b) a lithium component, and
  (c) a component of at least one element selected from the group consisting of iridium, manganese, scandium, magnesium, yttrium, ytterbium, lutecium, vanadium and chromium; and (B) catalyst component, which is supported on a separate carrier from said (A) catalyst component, being selected from the group consisting of
  (a) an iron component and a component of at least one element selected from the group consisting of iridium and palladium,
  (b) a molybdenum component and a component of at least one element selected from the group consisting of iridium and palladium,
  (c) an iron component, a molybdenum component and a component of at least one element selected from the group consisting of iridium and palladium, and
  (d) a copper component, alone or in combination with a component of at least one element selected from the group consisting of zinc and chromium; and said catalyst composition having a high selectivity of ethanol.

2. The process of claim 1 wherein the catalyst component (A) contains rhodium, lithium and manganese.

3. The process of claim 1 wherein the catalyst component (A) contains rhodium, lithium and scandium.

4. The process of claim 1 wherein the catalyst component (A) contains rhodium, lithium, manganese and iridium.

5. The process of claim 1 wherein the catalyst component (A) contains rhodium, lithium, scandium and iridium.

6. The process of claim 1 wherein the catalyst component (B) is the catalyst component (d).

7. The process of claim 1 wherein the catalyst component (A) contains rhodium, lithium and manganese and the catalyst component (B) is the catalyst component (d).

8. The process of claim 1 wherein the catalyst component (A) contains rhodium, lithium and scandium and the catalyst component (B) is the catalyst component (d). pg,51

9. The process of claim 1 wherein the catalyst component (A) contains rhodium, lithium, manganese and iridium and the catalyst component (B) is the catalyst component (d).

10. The process of claim 1 wherein the catalyst component (A) contains rhodium, lithium, scandium and iridium and the catalyst component (B) is the catalyst component (d).

* * * * *